United States Patent [19]

Perry

[11] Patent Number: 5,672,750
[45] Date of Patent: Sep. 30, 1997

[54] PREPARATION OF AROMATIC AMIDES FROM CARBON MONOXIDE, AN AMINE AND AN AROMATIC CHLORIDE

[75] Inventor: Robert James Perry, Pittsford, N.Y.

[73] Assignee: Eastman Chemical Company, Kingsport, Tenn.

[21] Appl. No.: 656,594

[22] Filed: May 31, 1996

Related U.S. Application Data

[63] Continuation of Ser. No. 357,897, Dec. 16, 1994, abandoned.

[51] Int. Cl.$^6$ .................... C07C 231/10; C07D 209/49
[52] U.S. Cl. ................... 564/132; 548/473; 558/415; 560/43; 564/162
[58] Field of Search ..................... 564/132, 162; 558/415; 560/43; 548/473

[56] References Cited

U.S. PATENT DOCUMENTS 5,159,113  10/1992  Nicholas ........................... 564/132

OTHER PUBLICATIONS

"Advanced Organic Chemistry", by J. March, John Wiley & Sons, Inc., New York, 1985.
Schoenberg, et al., in "Journal of Organic Chemistry", (1974) 39, 3327.
Huser, M. et al., "Angewante Chemie, International Edition", (1989) 28, 1386.
Grushin, V. V. et al., "Journal of the Chemical Society, Chemical Communications", (1992), 611.
Ben–David, Y. et al., "Journal of the American Chemical Society", (1989) 11, 8742.
Cassar, L. et al., "Journal of Organometallic Chemistry", (1973) 51, 381.
Brunet, J. J. et al., "Journal of Organic Chemistry", (1983) 48, 1166.
Foa, M. et al., "Journal of Organometallic Chemistry", (1985) 285, 293.
Kudo, K. et al., "Chemistry Letters", (1987), 577.
Scott, W. J., "Journal of the Chemistry Society, Chemical Communications", (1987), 1755.
Mutin, R. et al., "Journal of the Chemical Society, Chemical Communications", (1988), 896.
Bozell, J. J. et al., "Journal of the American Chemical Society", 110 (1988), 2655.

Primary Examiner—Shailendra Kumar
Attorney, Agent, or Firm—Harry J. Gwinnell; John D. Thallemer

[57] ABSTRACT

The present invention is directed to a process for preparing an aromatic amide. More specifically, the process involves reacting carbon monoxide, an amine and an aromatic chloride in the presence of an iodide or bromide salt, a catalyst, and a base.

23 Claims, No Drawings

PREPARATION OF AROMATIC AMIDES FROM CARBON MONOXIDE, AN AMINE AND AN AROMATIC CHLORIDE

This is a continuation of application Ser. No. 08/357,897 filed on Dec. 16, 1994, now abandoned.

FIELD OF THE INVENTION

This invention relates to a process for the preparation of aromatic amides.

BACKGROUND OF THE INVENTION

Aromatic amides may be prepared in variety of ways as described in "Advanced Organic Chemistry," by J. March, John Wiley & Sons, Inc., New York, 1985. However, the most common methods utilize the reaction between aromatic acids, or their derivatives, and a primary amine. The aromatic acid derivative used most often is an aromatic acid chloride which is hydrolytically sensitive. In some cases, the desired aromatic acid or derivative is not readily available. It would therefore be desirable to provide a process capable of producing a variety of aromatic amides which are not made from hydrolytically sensitive starting materials. It is also desirable to provide a method for producing aromatic amides from readily available, non-aromatic acid derived starting materials.

Schoenberg, et al., in "Journal of Organic Chemistry", (1974) 39, 3327 discloses the palladium catalyzed carbonylation and coupling reaction of aromatic iodides and bromides with primary amines in the presence of a base and a suitable solvent to give an amide product. This method, though, utilizes expensive aromatic iodides or bromides. It would therefore also be desirable to have a process which uses less expensive reagents to prepare aromatic amides, such as aromatic chlorides.

Huser, M. et al, "Angewante Chemie, International Edition", (1989) 28, 1386; Grushin, V. V. et al., "Journal of the Chemical Society, Chemical Communications", (1992), 611; and Ben-David, Y. et al., "Journal of the American Chemical Society", (1989) 111, 8742, teach that the use of strongly basic and sterically demanding ligands on palladium will induce carbonylation on aryl aromatic chlorides. Cassar, L. et al., "Journal of Organometallic Chemistry", (1973) 51, 381, teaches that nickel catalysts will allow carbonylation in some cases and Brunet, J. J. et al., "Journal of Organic Chemistry", (1983) 48, 1166; Foa, M. et al., "Journal of Organometallic Chemistry", (1985) 285, 293; and Kudo, K. et al., "Chemistry Letters", (1987), 577, teach that cobalt complexes sometimes work.

Scott, W. J., "Journal of the Chemical Society, Chemical Communications", (1987), 1755 and Mutin, R. et al., "Journal of the Chemical Society, Chemical Communications", (1988), 896, teach palladium catalyzed carbonylation reactions of chloroarenes using $Cr(CO)_3$. Bozell, J. J. et al., "Journal of the American Chemical Society", 110 (1988), 2655, teaches a palladium catalyzed carbonylation reaction of chloroarenes which requires both Ni and Pd catalysts and the presence of NaI.

Accordingly, what is needed is a process for preparing a wide variety of aromatic amides which utilizes a carbonylation and coupling reaction rather than the conventional condensation reaction between acid chloride and amines. Moreover, the process should allow the use of inexpensive aromatic chlorides instead of aromatic iodides or bromides or hydrolytically unstable acid chlorides.

SUMMARY OF THE INVENTION

The present invention is directed to a process for preparing an aromatic amide, said process comprising reacting:

(A) carbon monoxide;

(B) a primary or secondary amine having the structure:

wherein x is at least 1; R is selected from the group consisting of an alkyl group having 2 to 23 carbon atoms and an aryl group having 6 to 14 carbon atoms; and $R^1$ is selected from the group consisting of hydrogen, an alkyl group having 1 to 20 carbon atoms and an aryl group having 5 to 14 carbon atoms; and (C) an aromatic chloride having the following structure:

wherein y is 1, 2, or 3; z is at least 1; $R^2$ is selected from the group consisting of an alkyl group having 1 to 20 carbon atoms and an aryl group having 5 to 10 carbon atoms; and Ar is an aromatic nucleus, provided that either $R^2$ or Ar contains at least one electron withdrawing group in addition to the chlorine, said electron withdrawing group having a Hammett sigma constant with a value greater than 0.10 and excluding halogen, wherein said process is conducted in the presence of an iodide or bromide salt, a transition metal catalyst, and a base.

DESCRIPTION OF THE INVENTION

The process of the present invention for preparing aromatic amides involves reacting carbon monoxide (CO), a primary or secondary amine and an aromatic chloride. It is convenient to add an excess of carbon monoxide to the reaction. Carbon monoxide can be at or below atmospheric pressure or at a higher pressure. One can readily adjust the carbon monoxide pressure by pressurizing the reaction vessel with carbon monoxide to the desired reaction pressure. The carbon monoxide can be diluted with inert gases such as nitrogen or Argon.

The amine is a primary or secondary amine which is soluble or dispersible in the reaction mixture. The amine has the following structure:

wherein x is 1 or greater, preferably 1, 2, or 3; R is an alkyl group having 2 to 23, preferably 2 to 12 carbon atoms or an aryl group having 5 to 14, preferably 5 to 10 carbon atoms; and $R^1$ is hydrogen, an alkyl group having 1 to 20, preferably 1 to 10 carbon atoms or an aryl group having 5 to 14, preferably 5 to 10 carbon atoms. The amine may be a mono or polyfunctional amine. Polyfunctional amines include, but are not limited to difunctional amines, trifunctional amines and tetrafunctional amines. The aliphatic amines may contain one or two non-aryl rings or be acyclic. Preferably, the aliphatic amines are primary or secondary alkyl amines wherein the alkyl group has 5 to 10 carbon atoms. The alkyl groups can be branched or unbranched. Specific alkyl amines include methylamine, ethylamine, n-propylamine, isopropylamine, n-butylamine, n-octylamine, dodecylamine, cyclohexylamine, dimethylamine, diethylamine, diisopropylamine, dibutylamine, ethylisopropylamine, piperidine, morpholine, pyrrolidine, ethylenediamine, propylenediamine, piperazine and the like.

Useful amines also include aromatic amines having 5 to 14 carbon atoms, preferably 6 to 10 carbon atoms, and heteroaromatic amines having 5 to 14 carbon atoms, preferably 6 to 8 carbon atoms. Specific aromatic amines are aniline, o-toluidine, m-toluidine, p-toluidine, m-methoxyaniline, p-methoxyaniline, p-dimethylaminoaniline, p-aminomethylbenzoate, p-aminobenzonitrile, p-aminoacetophenone, 1-aminonaphthalene, 2-aminonaphthalene, and the like.

Specific polyfunctional amines include:

1,4-diaminobenzene

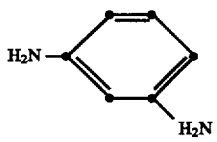

1,3-diaminobenzene

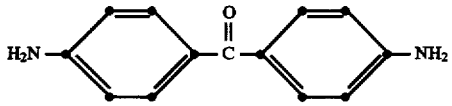

4,4'-diaminobenzophenone

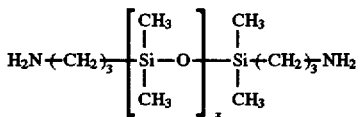

X = 1–50

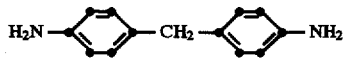

4,4'-diaminodiphenylmethane

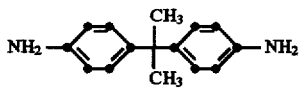

2,2-bis(4-aminophenyl)propane

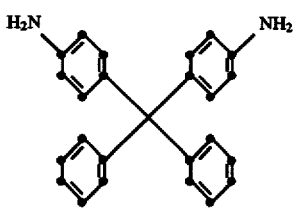

4,4'-diaminotetraphenylmethane

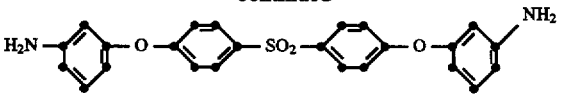

4,4'-bis(3-aminophenoxy)diphenylsulfone

2,2-bis[4-(4-aminophenoxy)phenyl]propane $$H_2N(CH_2)_yNH_2$$
$$y = 1-10$$

terminal diaminoalkane

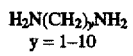

4,4'-diaminodiphenylether

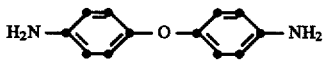

1,4-bis[2-(4-aminophenyl)propyl]benzene

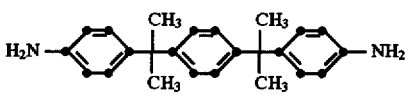

5-amino-3-(4-aminophenyl)-1,1,3-trimethylindane

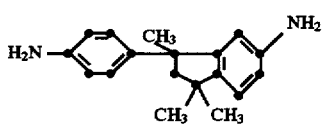

2,2'-bis(trifluoromethyl)-4,4'-diaminodiphenylether

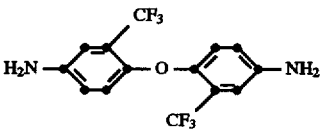

3,4'-diaminodiphenylether

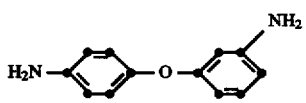

2,4,6-triaminotoluene

The aromatic chloride has the following structure:

wherein y is 1, 2, or 3; z is 1 or more; $R^2$ is an alkyl group having 1 to 20, preferably 1 to 10 carbon atoms or an aryl group having 5 to 10, preferably 5 to 10 carbon atoms; and Ar is an aromatic nucleus. Either the $R^2$ group or the aromatic nucleus Ar must contain at least one electron withdrawing group in addition to the chlorine. The electron withdrawing group cannot be a halogen and must have a Hammett sigma constant with a value greater than 0.10, preferably greater than 0.25. Preferred electron withdrawing groups are sulfone, ketone, ester, phthalimido, and nitrile. In the case where y is at least 2, the chloro radicals are bonded to an aromatic nucleus in non-ortho positions. It is preferred that the aromatic chloride compounds be free of groups which unduly retard reaction by steric hindrance or by lowering the activity of the catalyst.

Examples of suitable aromatic chlorides are monoaromatic chlorides, diaromatic chlorides, and polyaromatic chlorides. Preferred monoaromatic chlorides are:

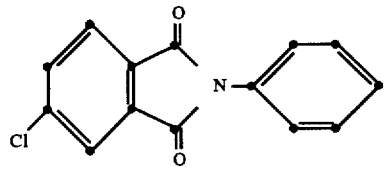

4-chloro-N-phenylphthalimide

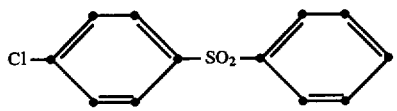

4-chlorodiphenylsulfone

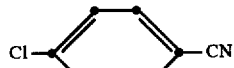

4-chlorobenzonitrile

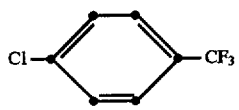

4-trifluoromethylchlorobenzene

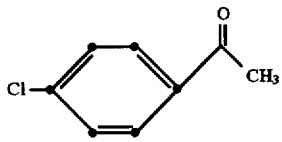

4-chloroacetophenone

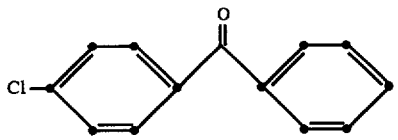

4-chlorobenzophenone

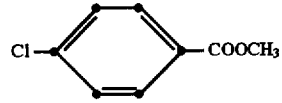

4-chloromethylbenzoate

4-chloronitrobenzene.

Preferred diaromatic and polyaromatic chlorides are: 4,4,-dichlorodiphenylsulfone, 4,4'-dichlorobenzophenone, 4,4'-dichloro-9,10-anthraquinone, 2,6-dichloro-9,10-anthraquinone, 2,7-dichloro-9,10-anthraquinone, and compounds having the structure

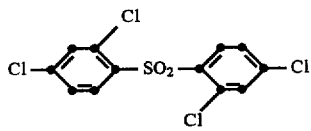

2,2',4,4'-tetrachlorodiphenylsulfone

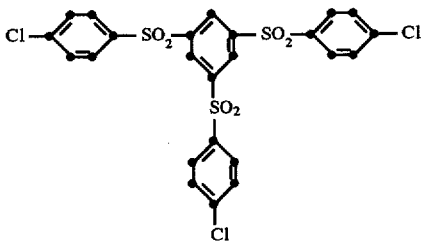

1,3,5-tris(4-chlorophenylsulfonyl)benzene.

Preferably, the process of the present invention for preparing an aromatic amide involves either reacting a monoamine with an aromatic monochloride, reacting a polyfunctional amine with an aromatic monochloride, or reacting a monoamine with an aromatic polyfunctional chloride.

The process proceeds well when the amine and chloro aromatic compounds are contacted in approximately stoichiometric amounts based on the number of reacting amino and chloro groups. However, it is not necessary to use stoichiometric quantities. An excess of a reactant can be used to drive the reaction toward completion. A convenient amount of excess preferably is used. In other words, one employs an amount of excess which provides the desired result, but which does not unduly hinder the process by adding unacceptable cost, or by complicating the process by making it unduly difficult to separate product from unreacted materials. When one of the organic reactants is used in excess, it is preferably used in an amount of from 1.001 to about 5 times the molar amount dictated by stoichiometry.

Although reactants are discussed herein as individual compounds, the process of the present invention is not limited to using individual compounds as reactants, but also includes using mixtures of compounds as reactants. It is desirable that the reactants not be subject to an unacceptable amount of undesirable side reactions to prevent the formation of an unacceptable amount of by-product. It is also desirable that the reactants be free of groups which unduly retard the reaction by, for example, stearic hindrance or lowering the activity of the catalyst.

In addition to carbon monoxide, an amine and an aromatic chloride, the process of the present invention is conducted in the presence of an iodide or bromide salt, a catalyst, and a base. The iodide or bromide salt is added in an amount of 0.01 to 5 equivalents based on the equivalents of aromatic chloride, more preferably in an amount of 0.25 to 2.5 equivalents based on the equivalents of aromatic chloride. While not wishing to be bound to any particular theory, the inventor believes that the iodide or bromide reacts with a neutral Pd(O) complex to form a more reactive anionic Pd(O) catalyst which more readily reacts with chloraromatic compounds. The iodide or bromide salt may be added as an inorganic salt such as LiI, NaI, KI, NaBr, KBr, LiBr or other dissociative iodide or bromide salt, or as an organic salt such as $R^3_3NH^+I^-$n, $R^3_4N^+I^-$, $R^3_3P^+I^-$ or $R^3_3NH^+Br^-$n, $R^3_4N^+Br^-$, $R^3_3P^+Br^-$ and the like, wherein $R^3$ is an aliphatic, aryl, or alkaryl group.

The catalyst for use in the present invention is a transition metal catalyst containing palladium, platinum and nickel compounds. The preferred catalyst is a palladium complex in the zero valent or divalent state. The palladium catalyst generally has one or more ligands bonded to one or more palladium atoms by ionic or covalent bonds. Simple palladium salts such as $PdX_2$, in which X is Cl, Br or I, can be used as the catalyst. Specific examples of other palladium catalysts are listed in Table I.

TABLE I

Palladium Catalysts
Palladium complexes in the divalent oxidation state:

| | |
|---|---|
| $PdX_2L_2$ | X = Cl, Br, or I |
| | L = $R^4{}_3P$, $R^4$ = alkyl or aryl group |
| $Pd(OAc)_2$ | OAc = acetate |
| $Pd(OAc)_2L_2$ | OAc = acetate |
| $PdCl_2(RCN)_2$ | $R^5$ = methyl or phenyl group |
| $PhPdXL_2$ | X = Br, Cl or I |
| $PdCl_2(COD)_2$ | COD = cis, cis-1,5-cyclooctadiene, |
| $Pd(acac)_2$ | acac = 2,4-pentanedionate |
| $PdCl_2DPPF$ | DPPF = 1,1'-bis(diphenylphosphino)-ferrocene |
| $PdCl_2DPPE$ | DPPE = 1,2-bis(diphenylphosphino)-ethane |
| $PdCl_2DPPP$ | DPPP = 1,3-bis(diphenylphosphino)-propane |
| $PdCl_2DPPB$ | DPPB = 1,4-bis(diphenylphosphino)-butane |

Palladium complexes in the zero valent oxidation state:

| | |
|---|---|
| $PdL_4$ | L = $R^4{}_3P$, $R^4$ = alkyl or aryl group |
| $Pd(DPPE)_2$ | DPPE = 1,2-bis(diphenylphosphino)-ethane |
| $Pd(DPPP)_2$ | DPPP = 1,3-bis(diphenylphosphino)-propane |
| $PD(DPPB)_2$ | DPPB = 1,4-bis(diphenylphosphino)-butane |

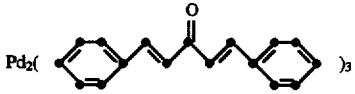

A catalytic amount of the catalyst is employed. The term "catalytic amount" refers to an amount of catalyst which catalyzes the reaction to the desired extent. Generally, the amount of catalyst is at least 0.005 equivalents based on the equivalents of aromatic chloride. Preferrably, the catalyst is present in an amount of 0.005 to 0.20, more preferrably 0.01 to 0.1 equivalents based on the equivalents of aromatic chloride. There is no upper or lower limit on the amount of catalyst other than cost and ease of separation of the catalyst from products and unreacted reactants. The catalyst can be bound to a support or unsupported.

Optionally, a ligand such as phosphine or arsine can be included in the process. Such ligands along with the transition metal catalyst increase the rate of the catalyzed reaction. The amount of ligand used is preferably 0.01 to 5.0 equivalents per equivalent of catalyst. More preferably, the amount of ligand used is about 2.0 equivalents per equivalent of catalyst. While not wishing to be bound by any theory, the present inventors believe that the ligand speeds up the oxidative addition of the catalyst by making the catalyst more nucleophilic.

A base is used in the process of the present invention to neutralize by-product hydrogen halide. Useful organic bases include tertiary amines having the formula $NR^5$ wherein each $R^5$ is independently selected from lower alkyl groups having from 2 to 6 carbon atoms. Specific tertiary amines are tributylamine, 1,3-diazobicyclo(5,4,0)-7-undecene (DBU), and 1,5-diazobicyclo(4,3,0)non-5-ene (DBN). The base can be immobilized on a cross-linked polymer such as cross-linked poly(vinylpyridine) beads. Generally, one employs at least enough base to react with the by-product hydrogen halide produced. Excess base can be used, however, excess base may slow the rate of reaction. The base is present in an amount of 0.1 to 100 equivalents based on the equivalents of aromatic chloride. Preferably, the base is present in ah amount of 0.5 to 10 equivalents, most preferably 1 to 5 equivalents, based on the equivalents of aromatic chloride.

The process of the present invention is optionally conducted in the presence of an organic solvent which appreciably dissolves both reactants to provide a liquid reaction medium and facilitates the contacting of the reactants and the catalyst. It is desirable that the organic solvent be "inert" to the reaction, i.e., that the solvent not enter into the reaction in an undesired way. Preferred organic solvents include hydrocarbon solvents having $C_5$–$C_{20}$, such as toluene and xylene; ether solvents characterized by R'OR' wherein R' is an aliphatic or aromatic hydrocarbon having $C_4$–$C_{10}$, such as tetrahydrofuran, diglyme (2-methoxyethyl ether), and glyme (1,2-dimethoxyethane); and dipolar aprotic solvents. Preferred dipolar aprotic solvents include: N,N-dimethylformamide, N,N-dimethylacetamide, dimethylsulfoxide, 1,3-dimethyl-2-imidazolidinone, hexamethylphosphoramide, N-methylpyrrolidinone, N-cyclohexylpyrrolidinone, dimethylimidazolidinone, and the like.

The amount of solvent present is not critical to the reaction, however, it is desirable to use enough solvent to facilitate the reaction. There is no theoretical upper limit on the amount of solvent employed, however, practical limits are imposed by the size of the reaction vessel, the ease of separation of product from the reaction medium, cost and other factors. Preferably, the amount of solvent used is 0.1 to 10,000 weight percent based on the weight of aromatic chloride. More preferably, the solvent is used in an amount of 1 to 5000 weight percent, most preferably 1000 to 5000 weight percent based on the weight of aromatic chloride.

The process of this invention is preferably conducted at a temperature within the range of 20° C. to 250° C. with agitation to facilitate the dissolution of carbon monoxide and reactants. More preferably, the temperature range is 70° C. to 200° C., and most preferably 90° C. to 125° C. Generally, temperatures above 250° C. should be avoided since decomposition of products or reactants may occur. At temperatures below 20° C., the rate of reaction is generally too slow.

The reaction time is from 0.1 to 100 hours, preferably 0.5 to 50 hours. The reaction time is dependent on such reaction parameters as the reactivity of the reactants, activity and amount of catalyst, reaction temperature, pressure and so forth.

The process of the present invention is used to prepare aromatic amides which are useful as intermediates in the preparation of pesticides, herbicides, pharmaceuticals and monomers.

The materials and testing procedures used for the results shown herein are as follows:

Reactions were performed in a 120 mL pressure reaction vessel containing a Teflon coated stir-bar, fitted with a pressure gauge, a pressure release valve, a gas inlet and a straight ball valve for degassing and sample withdrawal, in a well ventilated hood and behind safety shields. Reactions were monitored on an HP 5890 gas chromatograph using a 15 m, 0.25 μm DB-5 column, 0.32 mm i.d., and a flame ionization detector. Helium flow rate through the column was 4.0 mL/min.

The gas chromatograph parameters employed from analysis were as follows: injection port, 300° C.; detector, 350° C.; temperature ramp from 50° C. (hold 1 min) to 300° C. (hold 10 min) at 20° C./min $^1$H NMR and $^{13}$C NMR spectra were acquired on a 300 MHz spectrometer using CDCl$_3$ or DMSO-d$_6$ as both solvent and reference. $^{31}$P NMR spectra were acquired on a 120 MHz spectrometer using DMF-d$_7$ as solvent and H$_3$PO$_4$ as an external reference. Fourier transform infrared spectra were recorded as KBr pellets. Elemental analysis were obtained by combustion analysis.

The following chemicals were used in the reactions. Aniline (dried over CaH$_2$) and 1,8-diazabicyclo[5.4.0]undec-7-ene (DBU) were fractionally distilled under reduced pressure. Triphenylphosphine (PPh$_3$) was recrystallized from hexanes. NaI, KI and NaBr were dried at 120° C. in vacuo. CO, bis(triphenylphosphine)palladium(II)chloride (PdCl$_2$L$_2$), tetrakis(triphenylphosphine)palladium (PdL$_4$), tri(o-tolyl)phosphine, tri(p-tolyl)phosphine, 1,2-bis(diphenylphosphino)ethane (DPPE), N,N-dimethylacetamide (DMAc, anhydrous), tetra-n-butylammonium iodide, 4-chlorophenyl phenyl sulfone, 4-chlorobenzotrifluoride, methyl 4-chlorobenzoate, 1-chloro-4-fluorobenzene, 4-chlorotoluene, 4-chloroanisole, p-chlorobenzonitrile, 4'-chloroacetophenone, chlorobenzene, 4-chlorophthalic anhydride, and 4-chlorobiphenyl were used as received.

Preparation of Starting Materials:
(a) 4-iodophthalic anhydride 3,4-Dimethylaniline (121 g, 1.0 mol), ice/water mixture (1.5 L), and conc HCl (215 ml) were cooled to 0° C. then a solution of NaNO$_2$ (69 g, 1.0 mol) in water (100 mL) was added rapidly. The reaction was stirred for 30 min at 5° C., then water (500 mL) and KI(170 g, 1.02 mol) were added. The mixture was allowed to stir at room temperature for 18 hours. The aqueous layer was decanted from the heavy black layer and washed with CH$_2$Cl$_2$. The organic extract was combined with the black layer which was then washed with water. The organic layer was dried over MgSO4, concentrated and distilled (60° C./0.1 torr) to give 185 g (80%) 3,4-dimethyliodobenzene, as a reddish oil. This intermediate oil (185 g, 0.73 mol), pyridine (450 mL) and water 1.2 L) were heated to 80°–90° C. and then KMnO$_4$ (280 g, 1.8 mol) was added in portions over 3 hours (reaction was exothermic). Heating continued for 1 hour after addition was complete then the excess KMnO$_4$ was destroyed with EtOH.

The reaction mixture was filtered, then the excess pyridine removed by distillation. The aqueous layer was acidified with conc HCl, cooled and the solid collected by filtration. After washing extensively with water and drying, the yield of 4-iodophthalic acid, was 220 g (94%). The crude acid (220 g, 0.75 mol) was added over 30 minutes to warm (50° C.) AcCl (750 g). The mixture was heated to reflux. When dissolution was complete, the mixture was filtered, concentrated and cooled. The crystalline solid was washed with cold Et$_2$O then ligroin to give 125 grams (61%) product, mp 123°–125° C. $^1$H NMR(DMSO-d$_6$) δ7.99(s.1), 7.90 (d, J=8.1 Hz, 1), 7.48 (d, J=7.9 Hz, 1).

(b) 4-Chloro-N-phenylphthalimide

A solution of 4-chlorophthalic anhydride (9.12 g, 500 mmol), aniline (4.65 g, 50 mmol), pyridine (12.01 g, 152 mmol) and DMAc (40 mL) was heated at 70° C. for 1 hour under argon. Acetic anhydride (20.0 g, 196 mmol) was added and the solution was allowed to stir at 80° C. for a total of 4 hours. The reaction mixture was cooled to ca. 5° C. and the crystalline solid removed by filtration, washed with acetone and methanol and dried in vacuo to give 9.0 g (70%) product which was recrystallized from acetic anhydride, mp 187°–189° C., (liturature melting point) 189.5°–191° C. $^1$H NMR(CDCl$_3$) δ7.90 (d, J=1.6 Hz, 1), 7.88 (d, J=8.0 Hz, 1), 7.73 (dd, J=8.0, 1.6 Hz, 1), 7.50 (m, 2), 7.41 (m,3). $^{13}$C NMR (CDCl$_3$) {$^1$H} δ166.2, 165.9 141.1, 134.4, 133.5, 131.5, 129.9, 129.1, 128.2, 126.4, 124.9, 124.1.

(c) 4-Iodo-N-phenylphthalimide

As described above, 4-iodophthalic anhydride (2.0 g, 7.3 mmol), aniline (665 µL, 7.3 mmol), pyridine (2.1 mL, 25.5 mmol) and DMAc (10 mL) were heated at 80° C. for 2 hours, followed by continued heating in the presence of acetic anhydride (2.75 mL, 29.2 mmol) for 16 hours. MeOH (5 mL) was added to the warm solution which was then cooled to room temperature. The crystalline solid was removed by filtration, washed with MeOH and dried in vacuo to give 1.96 g (77%) product. The filtrate was concentrated and cooled to 0° C. to afford another 300 mg (11%) product. Total yield 88% mp 178°–179° C., $^1$H NMR (CDCl$_3$) δ8.27 (d, J=1.0 Hz, 1), 8.13 (dd, J=7.5, 1.0 Hz, 1), 7.65 (d, J=7.9 Hz, 1), 7.49 (m, 2), 7.40 (m, 3). $^{13}$C NMR (CDCl$_3$) {$^1$H} δ166.6, 165.7, 143.3, 133.1, 132.8, 131.5, 131.0, 129.1, 128.2, 126.4, 124.9, 101.1. Combustion analysis calculated for C$_{14}$H$_8$INO$_2$: C, 48.16; H, 2.31; N, 4.01. Found: C, 47.81; H, 2.39; N, 3.95.

The process of the present invention will be further illustrated by a consideration of the following examples, which are intended to be exemplary of the invention.

EXAMPLE 1

Low CO pressure and 1.2 equivalent of NaI.

A 120 mL pressure reaction vessel containing a stirring bar, a pressure gauge,-a pressure release valve, a gas inlet and a straight ball valve for degassing and sample withdrawal was charged with 566 mg (2.19 mmol) 4-chloro-N-phenylphthalimide, 200 µL (2.19 mmol) aniline, 46 mg (0.066 mmol) bis(triphenylphosphine) palladium (II) chloride, 35 mg (0.132 mmol) triphenylphosphine, 395 µL (2.6 mmol) 1,8-diazobicyclo [5.4.0]undec-7-ene, 395 mg (2.6 mmol) NaI and 15 mL DMAc. The reaction mixture was degassed, placed under 5 psig CO and heated to 115° C. Aliquots were removed at timed internals for gas chromatographic (GC) analysis to determine % completion of reaction. Results are summarized in Table II.

After 1 hour, GC analysis showed 95% completion of the reaction. In a separate reaction, run in an identical manner but stopped after 6 hours, an isolated yield of 82% of N-phenyl-4-(carboxyanilino) phthalimide was obtained having a melting point of 266.5°–268° C.; $^1$H NMR (DMSO-d$_6$) δ10.60 (s, 1), 8.50 (s,1), 8.41 (dd, J=7.5, 1.0 Hz, 1), 8.08 (d, J=7.78 (d, J=7.8 Hz, 2), 7.46 (m,5), 7.35 (t, J=7.8 Hz, 2), 7.11 (t, J=7.3 Hz, 1); and $^{13}$C NMR (DMSO-d$_6$) {$^1$H} δ166.3, 166,2, 163.4, 140.2, 138.5, 134.1, 133.6, 131.7, 131.6, 128.7, 128.4, 127.9, 127.1, 124.0, 123.4, 122.0, 120.5. Combustion analysis calculated for C$_{21}$H$_{14}$N$_2$O$_3$: C, 73.68; H, 4.12; N, 8.18. Found: C, 73.71; H,4.10; N, 7.94.

Comparative Example A

Example 1 was repeated without NaI.

In Example 1, 95% conversion was obtained after one hour as determined by GC analysis. However, in Comparative Example A, GC analysis indicated 58% after one hour. The test results are summarized in Table II.

Comparative Example B

Example 1 was repeated except with 95 psig CO instead of 5 psig CO.

In Example 1, 95% conversion was obtained after one hour as determined by GC analysis. However, in Comparative Example B, GC analysis indicated 71% after one hour. The test results are summarized in Table II.

Comparative Example C

Example 1 was repeated except with 95 psig CO and no NaI instead of 5 psig CO and 1.2 equivalents NaI.

In Example 1, 95% conversion was obtained after one hour as determined by GC analysis. However, in Comparative Example B, GC analysis indicated 14% after one hour. The test results are summarized in Table II.

TABLE II

Effect of CO pressure and iodide on amidation reaction.

| Time (hrs.) | Ex. 1 5 psig CO 1.2 NaI | Comp. Ex. C 95 psig CO | Comp. Ex. A 5 psig CO | Comp. Ex. B 95 psigCO 1.2 NaI |
|---|---|---|---|---|
| 0.0 | 0.000 | 0.000 | 0.000 | 0.000 |
| 0.15 | 46.100 | | | 19.900 |
| 0.17 | | 12.600 | 8.500 | |
| 0.4 | | 8.800 | | |
| 0.5 | 95.000 | | | |
| 0.67 | | 12.500 | 43.900 | |
| 0.75 | 94.200 | | | 64.700 |
| 1.0 | 94.600 | 14.000 | 57.900 | 71.000 |
| 1.5 | 94.500 | | 74.700 | 78.900 |
| 2.5 | 94.700 | | 85.200 | 86.700 |
| 4.0 | 94.700 | 28.600 | 88.900 | 89.800 |
| 5.5 | | 34.100 | 89.500 | |
| 6.0 | | | | 92.100 |
| 23.0 | 93.800 | 46.500 | 90.200 | 96.600 |

EXAMPLES 2–4

The procedure as set forth in Example 1 was followed except that the equivalent amount of NaI based on equivalent 4-chloro-N-phenylphthalimide was varied as set forth in Table III.

The test results in Table III indicate that the fastest and most complete reactions occur in the presence of more than 0.5 equiv. NaI.

TABLE III

Effect of iodide concentration on amidation reaction.

| Time (hrs) | Ex. 2 .11 NaI | Ex. 3 .55 NaI | Ex. 4 4.36 NaI | Ex. 1 1.2 NaI | Comp. Ex. A No NaI |
|---|---|---|---|---|---|
| 0.0 | 0.000 | 0.000 | 0.000 | 0.000 | 0.000 |
| 0.15 | 16.800 | 36.500 | 40.200 | 46.100 | |
| 0.17 | | | | | 8.500 |
| 0.3 | 36.300 | 44.200 | | 90.000 | |
| 0.4 | | | 93.400 | | |
| 0.5 | 46.600 | 54.900 | | 95.000 | |
| 0.67 | | | | | 43.900 |
| 0.75 | 70.200 | | | 94.200 | |
| 1.0 | 61.700 | 87.100 | 93.700 | 94.600 | 57.900 |
| 1.5 | | | 94.500 | | |
| 2.5 | 90.000 | 93.000 | 93.800 | 94.700 | 85.200 |
| 4.0 | | | | | 88.900 |
| 5.5 | | | | | 89.500 |
| 6.0 | | | 94.300 | | |
| 6.5 | 94.300 | 96.100 | | | |
| 22.5 | | | 96.000 | | |
| 23.0 | 95.400 | 96.800 | | | |

EXAMPLES 5–7

The procedure of Example 1 was followed except that the the type of halide salt was varied.

The data in Table IV indicates that the fastest reactions occur with an iodide salt and the next fastest with a bromide salt. Reactions using a chloride salt were much slower than iodide or bromide, but did show a slight increase in reaction rate as compared to Comparitive Example A with no added salt.

TABLE IV

Effect of halide on reaction.

| Time (hrs.) | Ex. 5 LiCl | Ex. 6 LiBr | Ex. 7 LiI |
|---|---|---|---|
| 0.000 | 0.000 | 0.000 | 0.000 |
| 0.080 | 1.000 | 1.000 | 19.600 |
| 0.170 | 17.600 | 12.500 | 36.700 |
| 0.250 | 27.100 | 38.600 | 68.100 |
| 0.400 | 48.300 | 69.700 | 88.900 |
| 0.670 | 74.500 | 84.100 | 88.500 |
| 1.000 | 86.700 | 87.800 | 88.400 |
| 1.500 | 90.100 | 88.700 | 89.100 |
| 2.500 | 91.500 | 88.500 | 88.000 |
| 4.500 | 92.400 | 89.600 | 90.200 |
| 8.000 | 92.700 | 90.800 | 92.100 |
| 25.000 | 95.200 | 92.600 | 94.000 |

EXAMPLES 8–23

Example 1 was repeated except 4-chlorodiphenylsulfone (555 mg, 2.19 mmol) was used instead of 4-chloro-N-phenylphthalimide. In addition, other variations from Example 1 and the test results are summarized in Table V. The reaction scheme was as follows:

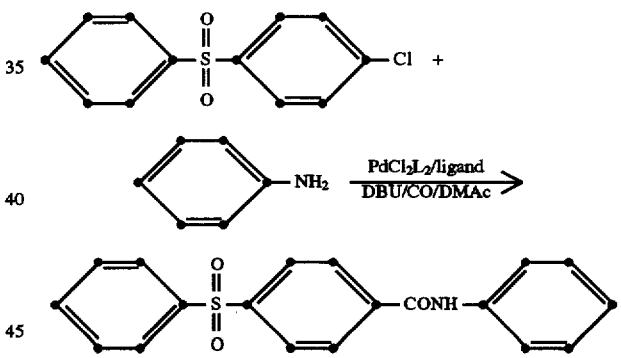

The data in Table V indicates that the best reaction conditions utilized 1,2-bis(diphenylphosphine) ethane as a ligand for the Pd catalyst, low CO presures and 1 equivalent of NaI.

TABLE V

| Ex. | Catalyst[a] (%) | Ligand[b] (%) | Salt (equiv.) | CO (psig) | Time (hrs.) | Product Yield[c] |
|---|---|---|---|---|---|---|
| 8 | 3 | 6 | — | 5 | 7 | 29 |
| 9 | 3 | 6 | — | 95 | 7 | 8 |
| 10 | 3 | 6 | 0.01 NaI | 5 | 22 | <2 |
| 11 | 3 | 6 | 0.01 NaI | 95 | 4 | 6 |
| 12 | 3 | 6 | 0.10 NaI | 5 | 32 | 50 |
| 13 | 3 | 6 | 0.10 NaI | 95 | 32 | 43 |
| 14 | 3 | 6 | 1.00 NaI | 95 | 19 | 57 |
| 15 | 3 | 6 | 1.00 NaI | 5 | 23 | 75 |
| 16 | 3 | 6 | 1.00 KI | 5 | 23 | 36 |
| 17 | 3 | 6 | 1.00 Bu$_4$N$^+$I$^-$ | 5 | 23 | 82 |
| 18 | 3 | 12 | 1.00 NaI | 5 | 19 | 88 |
| 19 | 3 | — | 1.00 NaI | 5 | 24 | 44 |

TABLE V-continued

| Ex. | Catalyst[a] (%) | Ligand[b] (%) | Salt (equiv.) | CO (psig) | Time (hrs.) | Product Yield[c] |
|---|---|---|---|---|---|---|
| 20 | 3 [g] | — | 1.00 NaI | 5 | 24 | 76 |
| 21 | 3 | 6[d] | 1.00 NaI | 5 | 23 | 15 |
| 22 | 3 | 6[e] | 1.00 NaI | 5 | 24 | 66 |
| 23 | 3 | 6[f] | 1.00 NaI | 5 | 24 | 98 |

[a]PdCl$_2$L$_2$(L = PPh$_3$)
[b]PPh$_3$
[c]yield of N-phenyl-4-(carboxyanilino) phthalimide as determined by GC.
[d]tri-o-tolylphosphine as ligand.
[e]tri-p-tolylphosphine as ligand.
[f]1,2-bis(diphenylphosphino)ethane as ligand.
[g]PdL$_4$.

EXAMPLE 24

Preparation of 4-carboxyanilino)diphenylsulfone.

A pressure bottle was charged with 4-chlorodiphenyl sulfone (1.387 g, 5.5 mmol), aniline (500 μL, 5.5 mmol), PdCl$_2$L$_2$, (116 mg, 0.16 mmol), DPPE (131 mg, 0.3 mmol), NaI (823 mg, 6.6 mmol), DBU (985 μL, 6.6 mmol) and DMAc (17 mL). The mixture was degassed and charged with 5 psig CO and then heated to 115° C. for 6 hours.

GC analysis of the reaction indicated all the starting material had been consumed. The solution was filtered through celite, concentrated in vacuo and then slurried with MeOH to give an off-white solid. The solid was washed extensively with MeOH and dried to give 1.54 grams product (83%). The filtrate was concentrated and subjected to chromatography on silica gel, eluting with 1:1, hexanes:EtOAc mixture to give an additional 147 mg (8%) product. Total yield was 91%, mp 206°–207.5° C. $^1$H NMR (CDCl$_3$) δ10.43 (s, 1), 8.09 (s, 4), 7.98 (d, J=8.0 Hz, 2), 7.65 (m,5), 7.33 (t, J=7.5 Hz, 2), 7.08 (t, J=7.0 Hz, 1). $^{13}$C NMR (CDCl$_3$) {$^1$H} δ164.2, 143.3, 140.6, 139.6, 138.7, 133.9, 129.8, 128.9, 128.6, 127.4, 124,0, 120.3. Combustion analysis calculated for C$_{19}$H$_{15}$NO$_3$S: C, 67.64; H, 4.48; N, 4.15. Found: C, 67.28; H, 4.60; N, 4.15. The test results are summarized in Table VI.

EXAMPLE 25

The procedure as described in Example 24 was repeated except the aromatic chloride, 4-chlorodiphenyl sulfone, was replaced with 4-chlorobenzonitrile to prepare 4-cyanobenzanilide.

After 17 hours reaction time, the reaction mixture was filtered, concentrated, dissolved in hot toluene and chromatographed on silica gel eluting with toluene. The product obtained was recrystallized from toluene to give 761 mg product (62%) mp 179.5°–180° C., lit mp 175°–176° C. $^1$H NMR (CDCl$_3$) δ8 10.45 (s, 1), 8.08 (d, J=8.3 Hz, 2), 8.03 (d, J=8.3 Hz, 2), 7.75 (d, J=8.0 Hz, 2), 7.34 (t, J=7.8 Hz, 2), 7.10 (t, J=7.3 Hz, 1). $^{13}$C NMR (CDCl$_3$) {$^1$H} δ164.1, 138.9, 138.7, 132.4, 128.6, 128.4, 124.0, 120.4, 118.4, 113.8. The test results are summarized in Table VI.

EXAMPLE 26

The procedure as described in Example 24 was repeated except the aromatic chloride, 4-chlorodiphenyl sulfone, was replaced with 4-chlorotrifluoromethylbenzene to prepare 4-trifluoromethylbenzanilide.

After recrystallization from toluene, as above, 1.136 grams (78%) product was obtained having amp of 202°–203° C., (liturature mp 198° C.) $^1$H NMR (CDCl$_3$) δ10.44 (s,1), 8.12 (d, J=8.2 Hz, 2), 7.88 (d, J=8.2 Hz, 2), 7.75 (d, J=7.9 Hz, 2), 7.34 (t, J=7.8 Hz, 2), 7.10 (t, J=7.4 Hz, 1). The test results are summarized in Table VI.

EXAMPLE 27

The procedure as described in Example 24 was repeated except the aromatic chloride, 4-chlorodiphenyl sulfone, was replaced with 4-chloroacetophenone to prepare 4-acetylbenzanilide.

After recrystallization from toluene, as above, 933 mg (71%) product was obtained having amp 197°–198° C. (liturature mp 188°–189° C. $^1$H NMR (CDCl$_3$) δ10.40 (s,1), 8.05 (s, 4), 7.77 (d, J=8.1 Hz, 2), 7.34 (t, J=7.8 Hz, 2), 7.09 (t, J=7.3 Hz, 1), 2.61 (s, 3). $^{13}$C NMR (CDCl$_3$) {$^1$H} δ197.6, 164.7, 138.9, 138.8, 138.7, 128.6, 128.1, 127.9, 123.9, 120.4, 26.9. The test results are summarized in Table VI.

EXAMPLE 28

The procedure as described in Example 24 was repeated except the aromatic chloride, 4-chlorodiphenyl sulfone, was replaced with 4-chlorobenzophenone to prepare 4-benzoylbenzanilide.

After recrystallization from toluene, as above, 1.351 grams (82%) product was obtained having amp of 161°–161.5° C. $^1$H NMR (CDCl$_3$) δ10.44 (s, 1), 8.08 (d, J=8.2 HZ, 2), 7.83 (d, J=8.2 HZ, 2), 7.77 (m, 4), 7.69 (t, J=7.5 Hz, 1), 7.56 (t, J=7.5 Hz, 2), 7.34 (t, J=7.8 Hz, 2), 7.10 (t, J=7.3 Hz, 1). $^{13}$C NMR (CDCl$_3$) {$^1$H} δ195.3, 164.7, 139.4, 138.9, 138.2, 136.6, 133.0, 129.6, 129.4, 128.6, 127.8, 123.5, 120.4. Combustion analysis calculated for C$_{20}$H$_{15}$NO$_2$: C, 79.72; H, 5.02; N, 4.65. Found: C, 79.53; H, 5.15; N, 4.65. The test results are summarized in Table VI.

EXAMPLE 29

The procedure as described in Example 24 was repeated except the aromatic chloride, 4-chlorodiphenyl sulfone, was replaced with 4-chloromethylbenzoate to prepare 4-carbomethoxybenzanilide.

After recrystallization from toluene, as above, 821 mg (59%) product was obtained having amp of 191.5°–192° C. (liturature melting point 192°–193° C.). $^{11}$H NMR (CDCl$_3$) δ10.41 (s, 1), 8.05 (s, 4), 7.77 (d, J=8.0 Hz, 2), 7.38 (t, J=7.8 Hz, 2), 7.09 (t, J=7.3 Hz, 1), 3.86 (s, 3). $^{13}$C NMR (CDCl$_3$) {$^1$H} δ165.6, 164.6, 139.0, 138.8, 132.0, 129.1, 128.6, 128.0, 123.9, 120.4, 52.3. The test results are summarized in Table VI.

EXAMPLE 30

The procedure as described in Example 24 was repeated except the aromatic chloride, 4-chlorodiphenyl sulfone, was replaced with 4-chlorofluorobenzene to prepare 4-fluorobenzanalide. GC indicated incomplete reaction and the product was not isolated. The test results are summarized in Table VI.

EXAMPLE 31

The procedure as described in Example 24 was repeated except the aromatic chloride, 4-chlorodiphenyl sulfone, was replaced with 4-chlorobenzene to prepare benzanalide. GC indicated incomplete reaction and the product was not isolated. The test results are summarized in Table VI.

EXAMPLE 32

The procedure as described in Example 24 was repeated except the aromatic chloride, 4-chlorodiphenyl sulfone, was replaced with 4-chlorobiphenyl to prepare 4-phenylbenzanalide. GC indicated incomplete reaction and the product was not isolated. The test results are summarized in Table VI.

EXAMPLE 33

The procedure as described in Example 24 was repeated except the aromatic chloride, 4-chlorodiphenyl sulfone, was replaced with 4-chlorotoluene to prepare 4-methylbenzanalide. GC indicated incomplete reaction and the product was not isolated. The test results are summarized in Table VI.

EXAMPLE 34

The procedure as described in Example 24 was repeated except the aromatic chloride, 4-chlorodiphenyl sulfone, was replaced with 4-chloroanisole to prepare 4-methoxybenzanalide. GC indicated no reaction. The test results are summarized in Table VI.

TABLE VI

Effect of substituent on amidation reaction.

| Ex. | Y | $\sigma_p{}^a$ | Yield$^b$ (%) |
|---|---|---|---|
| 24 | SO$_2$Ph | 0.67$^c$ | 91 |
| 25 | CN | 0.66 | 62 |
| 26 | CF$_3$ | 0.54 | 78 |
| 27 | COMe | 0.50 | 71 |
| 28 | COPh | 0.46 | 82 |
| 29 | COOMe | 0.39 | 59 |
| 30 | F | 0.06 | <15% conversion |
| 31 | H | 0.00 | <3% conversion |
| 32 | Ph | −0.01 | <12% conversion |
| 33 | Me | −0.17 | <1% conversion |
| 34 | OMe | −0.27 | 0 |

$^a$Hammett para substituent constants.
$^b$isolated, purified yields.
% conversion was determined by GC and products were not isolated.
$^c$estimated from Hammett meta constant.

The results in Table VI clearly indicate that the aromatic chloride must contain an electron withdrawing group in order for the amidation reaction to occur with high yields.

The process of the present invention allows for the preparation of a variety of aromatic amides using inexpensive aromatic chlorides reacted with amines in the presence of carbon monoxide and a bromide or iodide salt and a transition metal catalyst to result in unexpectedly faster aromatic amide formation rates than without added iodide or bromide salts.

Many variations will suggest themselves to those skilled in this art in light of the above detailed description. All such obvious modifications are within the full intended scope of the appended claims.

What is claimed is:

1. A process for preparing an aromatic amide, said process comprising reacting:

(A) carbon monoxide;

(B) a primary or secondary amine having the structure:

$$R\text{+\!NH}\!\!\!\phantom{x}_x^{R^1}$$

wherein x is 1, 2 or 3; R is selected from the group consisting of an alkyl group having 2 to 23 carbon atoms and an aryl group having 6 to 14 carbon atoms; and $R^1$ is selected from the group consisting of hydrogen, an alkyl group having 1 to 20 carbon atoms and an aryl group having 5 to 14 carbon atoms; and (C) an aromatic chloride having the following structure:

$$R^2\text{+\!Ar(Cl)}_y]_z$$

wherein y is 1, 2, or 3; z is 1 or 2; $R^2$ is selected from the group consisting of an alkyl group having 1 to 20 carbon atoms and an aryl group having 5 to 10 carbon atoms; and Ar is an aromatic nucleus, provided that either $R^2$ or Ar contains fat least one electron withdrawing group in addition to the chlorine, said electron withdrawing group having a Hammett sigma constant with a value greater than 0.10 and excluding halogen, wherein said process is conducted at less than 30 psig carbon monoxide in the presence of an iodide salt, a transition metal catalyst, and a base, provided that the iodide salt is present in an amount of 0.01 to 5 equivalents based on the equivalents of aromatic chloride, the transition metal catalyst is present in an amount of 0.005 to 0.2 equivalents based on the equivalents of aromatic chloride, and the base is present in an amount of 0.1 to 100 equivalents based on the equivalents of aromatic chloride.

2. The process of claim 1 wherein the iodide salt is present in an amount of 0.25 to 2.5 equivalents based on the equivalents of aromatic chloride, the transition metal catalyst is present in an amount of 0.01 to 0.1 equivalents based on the equivalents of aromatic chloride, the base is present in an amount of 0.5 to 10 equivalents based on the equivalents of aromatic chloride, and the organic solvent is present in an amount of 1 to 5000 weight percent based on the weight of aromatic chloride.

3. The process of claim 2 wherein the base is present in an amount of 1 to 5 equivalents based on the equivalents of aromatic chloride, and the organic solvent is present in an amount of 1000 to 5000 weight percent based on the weight of aromatic chloride.

4. The process of claim 1 wherein the electron withdrawing group is selected from the group consisting of sulfone, ketone, ester, phthalimido, and nitrile.

5. The process of claim 1 wherein the amine is a monoamine selected from the group consisting of methylamine, ethylamine, n-propylamine, isopropylamine, n-butylamine, n-octylamine, dodecylamine, cyclohexylamine, dimethylamine, diethylamine, diisopropylamine, dibutylamine, ethylisopropylamine, piperidine, morpholine, pyrrolidine, aniline, o-toluidine, m-toluidine, p-toluidine, m-methoxyaniline, p-methoxyaniline, p-dimethylaminoaniline, p-aminomethylbenzoate, p-aminobenzonitrile, p-aminoacetophenone, 1-aminonaphthalene, 2-aminonaphthalene, and combinations thereof.

6. The process of claim 1 wherein the amine is a polyfunctional amine selected from the group consisting of

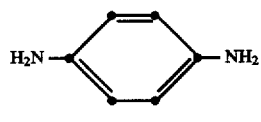

1,4-diaminobenzene,

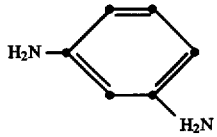

1,3-diaminobenzene,

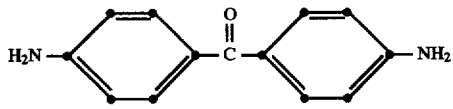

4,4'-diaminobenzophenone,

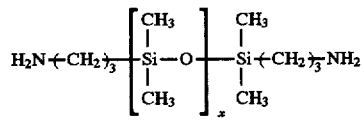

X = 1–50 bis(3-aminopropyl)tetramethyldisiloxane for x=1,

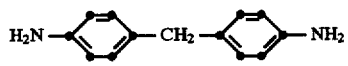

4,4'-diaminodiphenylmethane,

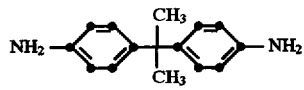

2,2-bis(4-aminophenyl)propane,

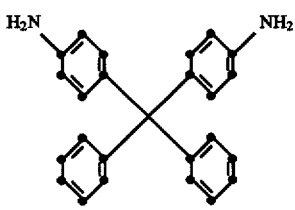

4,4'-diaminotetraphenylmethane,

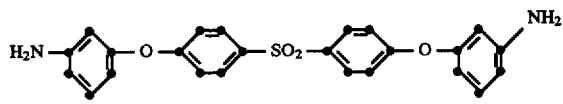

4,4'-bis(3-aminophenoxy)diphenylsulfone,

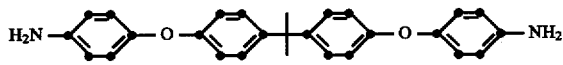

2,2-bis[4-(4-aminophenoxy)phenyl]propane,

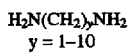
y = 1–10 terminal diaminoalkane,

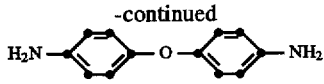

4,4'-diaminodiphenylether,

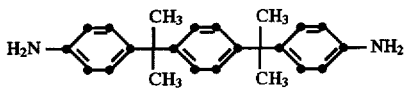

1,4-bis[2-(4-aminophenyl)propyl]benzene,

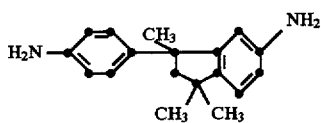

5-amino-3-(4-aminophenyl)-1,1,3-trimethylindane,

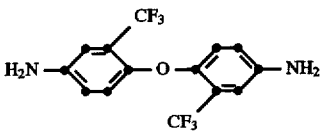

2,2'-bis(trifluoromethyl)-4,4'-diaminodiphenylether,

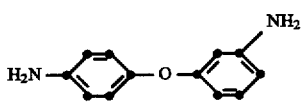

3,4'-diaminodiphenylether,

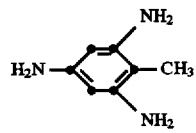

2,4,6-triaminotoluene, ethylenediamine, propylenediamine, piperazine, and combinations thereof.

7. The process of claim 6 wherein the amine is aniline.

8. The process of claim 1 wherein the aromatic chloride is a monoaromatic chloride selected from the group consisting of

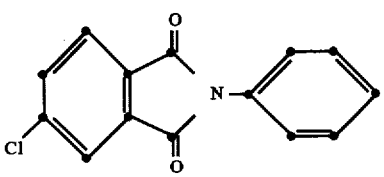

4-chloro-N-phenylphthalimide,

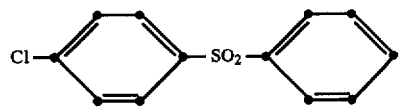

4-chlorodiphenylsulfone,

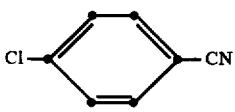

4-chlorobenzonitrile,

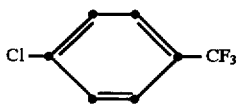

4-trifluoromethylchlorobenzene,

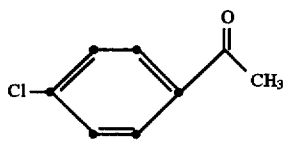

4-chloroacetophenone,

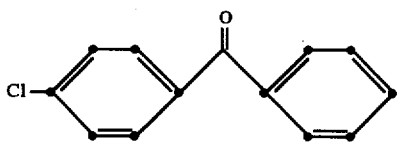

4-chlorobenzophenone,

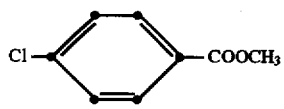

4-chloromethylbenzoate,

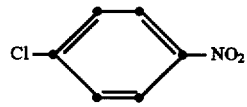

4-chloronitrobenzene, 4-chloronitrobenzene, and combinations thereof.

9. The process of claim 1 wherein the aromatic chloride is a polyaromatic chloride selected from the group consisting of 4,4'-dichlorodiphenylsulfone, 4,4'-dichlorobenzophenone, 4,4'-dichloro-9,10-anthraquinone, 2,6-dichloro-9,10-anthraquinone, 2,7-dichloro-9,10-anthraquinone, and compounds having the structure

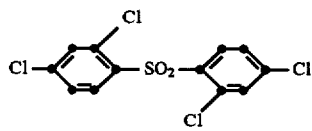

2,2',4,4'-tetrachlorodiphenylsulfone

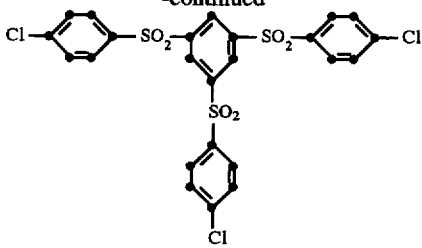

1,3,5-tris(4-chlorophenylsulfonyl)benzene and combinations thereof.

10. The process of claim 1 wherein the iodide salt is selected from the group consisting of sodium iodide, lithium iodide, potassium iodide, magnesium iodide, and calcium iodide or other dissociative iodide salts.

11. The process of claim 10 wherein the iodide salt is sodium iodide.

12. The process of claim 1 wherein the catalyst is selected from the group consisting of platinum, nickel, and palladium complexes.

13. The process of claim 12 wherein the palladium complex is a palladium salt having the formula $PdX_2$ wherein X is Cl, Br or I.

14. The process of claim 13 wherein the palladium complex is bis(triphenylphosphene)palladium(II) chloride.

15. The process of claim 1 which additionally contains a ligand in an amount of 0.01 moles to 5 moles per mole of transition metal catalyst.

16. The process of claim 15 wherein said ligand is 1,2-diphenylphosphine ethane.

17. The process of claim 1 wherein the base is selected from the group consisting of tertiary amines, $NR_3$ wherein R is independently selected from lower alkyl groups having 2 to 6 carbon atoms, and combinations thereof.

18. The process of claim 17 wherein the base is a tertiary amine selected from the group consisting of tributylamine, 1,3-diazobicyclo(5,4,0)-7-undecene, 1,5-diazobicyclo(4,3,0)non-5-ene, and combinations thereof.

19. The process of claim 1 which additionally contains an organic solvent in an amount of 0.1 to 10,000 weight percent based on the weight of aromatic chloride.

20. The process of claim 19 wherein the organic solvent is selected from the group consisting of hydrocarbon solvents having $C_5$–$C_{20}$, ether solvents characterized by R'OR' wherein R' is an aliphatic or aromatic hydrocarbon having $C_4$–$C_{10}$, and dipolar aprotic solvents.

21. The process of claim 20 wherein the organic solvent is a dipolar aprotic solvent.

22. The process of claim 21 wherein the dipolar aprotic solvent is selected from the group consisting of N,N-dimethylformamide, N,N-dimethylacetamide, dimethylsulfoxide, 1,3-dimethyl-2-imidazolidinone, hexamethylphosphoramide, N-methylpyrrolidinone, N-cyclohexylpyrrolidinone, dimethylimidazolidinone, and mixtures thereof.

23. The process of claim 22 wherein the dipolar aprotic solvent is N,N-dimethylacetamide.

* * * * *